(12) United States Patent
Kirsch et al.

(10) Patent No.: US 11,243,183 B2
(45) Date of Patent: Feb. 8, 2022

(54) GALVANIC OXYGEN SENSOR FOR MEASUREMENT IN GAS MIXTURES

(71) Applicant: IT Dr. Gambert GmbH, Wismar (DE)

(72) Inventors: Uwe Kirsch, Zierow (DE); Kerstin Wex, Alt Meteln (DE)

(73) Assignee: IT DR. GAMBERT GMBH, Wismar (DE)

(*) Notice: Subject to any disclaimer, the term of this patent is extended or adjusted under 35 U.S.C. 154(b) by 0 days.

(21) Appl. No.: 14/905,058

(22) PCT Filed: Jul. 14, 2014

(86) PCT No.: PCT/EP2014/065015
§ 371 (c)(1),
(2) Date: Jan. 14, 2016

(87) PCT Pub. No.: WO2015/007675
PCT Pub. Date: Jan. 22, 2015

(65) Prior Publication Data
US 2016/0153927 A1    Jun. 2, 2016

(30) Foreign Application Priority Data

Jul. 15, 2013 (DE) .......................... 102013011773.9

(51) Int. Cl.
*G01N 27/404* (2006.01)
*G01N 27/413* (2006.01)
*G01N 33/00* (2006.01)

(52) U.S. Cl.
CPC ......... *G01N 27/404* (2013.01); *G01N 27/413* (2013.01); *G01N 33/0059* (2013.01)

(58) Field of Classification Search
CPC ................. G01N 33/0059; G01N 27/406–41
See application file for complete search history.

(56) References Cited

U.S. PATENT DOCUMENTS 3,223,597 A * 12/1965 Hersch ..................... G01N 1/38
                                                                    205/783
3,223,608 A * 12/1965 Hersch ................ G01N 27/404
                                                                    204/431

(Continued)

FOREIGN PATENT DOCUMENTS

CN         85107581 A      4/1987
CN         2241341 Y      11/1996

(Continued)

OTHER PUBLICATIONS

Oxford et al. (Understanding the effect of halide poisoning in CO oxidation over Au/TiO2, Applied Catalysis A: General, 339 (2008) 180-186).*

(Continued)

*Primary Examiner* — Joshua L Allen
(74) *Attorney, Agent, or Firm* — Buchanan Ingersoll & Rooney PC

(57) ABSTRACT

The invention relates to an RoHS-compliant galvanic oxygen sensor of a new type. Said RoHS-compliant galvanic oxygen sensor has a lead-free anode, preferably is backwards compatible with the existing lead-containing sensors in the remaining electrical and geometric specification and the service life of the RoHS-compliant galvanic oxygen sensor, and has no cross-sensitivity to nitrous oxide. The RoHS-compliant galvanic oxygen sensor having a lead-free anode comprises a housing (1), a tin-containing anode (2), a diffusion barrier (3), a cathode (4), and an alkaline electrolyte (6). An aqueous solution of metal salts is used as the electrolyte, wherein a catalyst poison preferably is added to the electrolyte.

17 Claims, 4 Drawing Sheets

(56) References Cited

U.S. PATENT DOCUMENTS

| | | | | |
|---|---|---|---|---|
| 3,291,705 | A * | 12/1966 | Hersch | G01N 27/404 205/783 |
| 3,515,658 | A * | 6/1970 | Amdur | G01N 27/404 204/415 |
| 4,085,024 | A * | 4/1978 | Lawson | G01N 27/404 204/432 |
| 4,172,208 | A * | 10/1979 | Crutchfield | C07D 307/24 560/176 |
| 4,272,349 | A * | 6/1981 | Furutani | G01N 27/4077 204/429 |
| 4,279,974 | A * | 7/1981 | Nishio | G01N 27/4073 429/104 |
| 4,495,051 | A * | 1/1985 | Fujita | G01N 27/404 204/408 |
| 5,215,644 | A | 6/1993 | Ashikaga | |
| 2004/0100290 | A1 * | 5/2004 | Pope | B01J 19/0046 324/693 |
| 2004/0128088 | A1 | 7/2004 | Laletin et al. | |
| 2005/0279646 | A1 * | 12/2005 | Hasegawa | G01N 27/4166 205/789 |
| 2007/0272553 | A1 * | 11/2007 | Gambert | G01N 27/404 204/431 |
| 2011/0251447 | A1 * | 10/2011 | Cheung | B01J 21/04 585/262 |

FOREIGN PATENT DOCUMENTS

| | | | | |
|---|---|---|---|---|
| DE | | 41 35 824 | 6/1992 | |
| DE | 10 2006 024 022 | | 11/2007 | |
| GB | | 1 255 353 | 12/1971 | |
| JP | | H05-335032 | 12/1993 | |
| WO | | WO 99/22229 | 5/1999 | |
| WO | | WO-9922229 A1 * | 5/1999 | G01N 27/404 |
| WO | WO-2013039414 A1 * | | 3/2013 | G01N 27/404 |

OTHER PUBLICATIONS

Desikan et al. (Catalytic hydrodesulphurization of thiophene, Can. J. Chem., 42 (1964) 843-850).*
Bard et al. (AJ Bard, LR Faulkner, Electrochemical Methods: Fundamentals and Applications, Wiley, 2001, 2nd Ed, pp. 808-810). (Year: 2001).*
International Search Report dated Oct. 23, 2014, in corresponding PCT Application No. PCT/EP2014/065015.
German Office Action dated Jun. 10, 2014, in corresponding German Application No. 10 2013 011 773.9.
German Office Action dated Dec. 21, 2015, in corresponding German Application No. 10 2013 011 773.9.
Decision to Grant dated Apr. 19, 2016, in corresponding German Application No. 10 2013 011 773.9.
Office Action dated Jun. 19, 2017 by the State Intellectual Property Office of People's Republic of China in corresponding Chinese Patent Application No. 201480040622.5 and an English Translation of the Office Action. (14 pages).
Office Action dated Jul. 17, 2017, by the European Patent Office in corresponding European Patent Application No. 14 753 212.1. (4 pages).
Second Office Action dated Mar. 2, 2018 by the State Intellectual Property Office of People's Republic of China in corresponding Chinese Patent Application No. 201480040622.5 and an Englisn Translation of the Office Action. (4 pages).
Third Office Action dated Sep. 10, 2018 by the State Intellectual Property Office of People's Republic of China in corresponding Chinese Patent Application No. 201480040622.5 and an English Translation of the Office Action. (16 pages).

* cited by examiner

GALVANIC OXYGEN SENSOR FOR MEASUREMENT IN GAS MIXTURES

CROSS-REFERENCE TO RELATED APPLICATIONS

This application is a U.S. National Phase Application pursuant to 35 U.S.C. § 371 of International Patent Application No. PCT/EP2014/065015, filed on Jul. 14, 2014, and published as WO 2015/007675 on Jan. 22, 2015, which claims the benefit of German Patent Application No. 102013011773.9, filed on Jul. 15, 2013, the entireties of which are incorporated herein by reference for all purposes.

The invention generally relates to a galvanic oxygen sensor for measurement in gas mixtures. The invention relates in particular to an oxygen sensor which fulfils the requirements of the European RoHS regulations (2002/95/EG(ROHS-I) and the standard 2011/65/EU (RoHS II) and is preferably backwards compatible with existing lead-containing sensors in view of its electrical and/or geometric specification. Moreover, the invention relates preferably to an oxygen sensor which has preferably no cross-sensitivity to nitrous oxide.

BACKGROUND OF THE INVENTION

Because of their reliability and their small overall size and having a favorable cost-performance ratio, galvanic oxygen sensors are used to a considerable extent in industrial metrology, environmental metrology and medical metrology. Since their development in the 1950ies, a plurality of devices and measuring instruments have been developed for measuring the oxygen partial pressure, wherein said devices and measuring instruments are partly still used today and employ these kinds of sensors. Also in modern devices such as ventilators, emission measuring devices and automobile exhaust gas measuring devices, sensors of this kind are still used today preferably for oxygen measurement.

The sensors mostly comprise a housing, a cathode, an anode having a larger surface than the cathode, a diffusion barrier, an electrolyte and contact wires for electrical contact between cathode and anode. The anode supplies the necessary electrochemical potential for the reduction of the oxygen at the cathode. Galvanic sensors are described, e.g., in the U.S. Pat. Nos. 3,767,552 and 3,429,796.

In practice, lead has proved its superiority as anode material. It has a high hydrogen overvoltage and, therefore, is to a large extent corrosion-resistant in alkaline and slightly acid electrolytes over a large temperature range. The relatively high density of the lead allows small anode designs. Moreover, being a soft metal, it can be processed easily and is available with a high purity at relatively low cost.

For some years, lead, in addition to other heavy metals such as cadmium, mercury and chromium, has been discredited more and more. Already in relatively small doses and when acting chronically, lead has a damaging effect in the human organism on the nervous and blood-forming systems as well as the kidneys. The limiting values for lead and lead compositions in the environment therefore have been reduced more and more during the past years.

Since Jun. 1, 2006, the European standard (RoHS 2002/95/EG, the abbreviation RoHS means "Restriction of the use of certain Hazardous Substances") allows only minimum traces of these substances in electrical and electronic devices. For lead, the lower limit of the still allowed amount is 0.1% of the homogeneous material. This standard has been updated on Jun. 8, 2011. The standard 2011/65/EU, also called RoHS-II, broadens the field of application of the substance prohibitions in several steps. Starting from 2019, they will apply to all electrical and electronic devices which are not explicitly excluded. Starting from Jul. 22, 2014, also medical devices and monitoring and controlling devices are covered by this regulation.

In particular, the following substances are covered by the restrictions according to section 4 subsection 1, wherein admissible maximum concentrations in homogeneous materials are listed as follows in exhibit II in weight-percent: lead (0.1%); mercury (0.1%); cadmium (0.01%); hexavalent chromium (0.1%); polybrominated biphenyls (PBB) (0.1%) and polybrominated diphenyl ethers (PBDE) (0.1%).

Among measuring device manufacturers and their suppliers, this regulation widely led to the development of conforming, i.e. almost heavy metal-free products. Since also further heavy metals such as, e.g., cadmium and mercury are covered by these "heavy metal regulations", these metals are no alternative for the use in electrochemical oxygen sensors. The manufacturers of such sensors therefore have developed different approaches for solving this problem.

Amperometric sensors are widespread for the measurement of gases such as, e.g., carbon monoxide, nitrogen oxides and hydrogen sulfide. Predominantly three electrodes are used therein. A potentiostatic circuit, which is firmly connected to the sensor, maintains a constant potential between the working electrode and the reference electrode. For this purpose, the potentiostat must be supplied by a power supply source in the measuring device or by a battery integrated in the potentiostatic circuit. Carbon in combination with precious metals is typically used as electrode material. Therefore, such sensors fulfill the requirements of the RoHS regulation. Oxygen sensors according to this principle are offered, e.g., by the company Membrapor under the trade name O2/M-100 and the company City Technology under the trade name 4OXeco LP. This principle is disadvantageous since it is necessary to supply the sensor with power. This power supply prevents the backward compatibility with galvanic oxygen sensors. Also disadvantageous is the adaptation time of several hours after installation in the measuring device.

US 2008/0274401 also describes an amperometric, RoHS-compliant oxygen sensor. In this sensor, a bias voltage is applied by means of a button cell battery integrated in the sensor with the aid of a third electrode. Said bias voltage must be maintained exactly during the service life of the sensor. Moreover, it must be guaranteed in view of construction that no oxygen reaches the reference electrode because otherwise the bias voltage collapses and then no reliable measurement is possible any longer. Because of the battery in the sensor, the third electrode and the necessary shielding of the reference electrode from oxygen, the construction of such a sensor requires a substantially more involved design of the sensor and the sensor board than in galvanic oxygen sensors. This increases the manufacturing costs considerably. Like galvanic sensors, this sensor has a limited service life due to the capacity of the battery. Said service life can be limited considerably because of a high power consumption of the sensor. A further drawback as compared to galvanic sensors can be the worse electromagnetic compatibility of the sensor caused by the integrated electronic circuit. This can entail additional measures for shielding the sensor in the measuring device.

In addition to the most widespread lead anodes in galvanic oxygen sensors, anode materials without poisonous heavy metals have been used for some time.

GB patent 1 255 353 describes a galvanic oxygen sensor the anode material of which can consist, in addition to lead, of tin, copper and alloys thereof. The electrolyte of this sensor consists of or comprises sulfides. This arrangement leads to very stable sensor signals, which can be easily amplified electronically. However, it is a considerable disadvantage of this arrangement that the sensor cannot be used in environments containing acid gases such as, e.g., carbon dioxide. In this case, poisonous hydrogen sulfide would be released. Therefore, a medical-technical application is not possible.

GB patent 1 391 168 describes a device for measuring oxygen. The specific design comprising two oxygen-permeable membranes, one thereof being porous, a cathode made of silver and a tubular tin anode allows the measurement of oxygen in condensed media or in environments containing water droplets such as, e.g., respiratory gas humidifiers. Because of its hydrophobic character, the porous membrane prevents the formation of a closed water film on the surface, which might lead to a signal reduction. The composition of the electrolyte is not described. The art of combining two oxygen-permeable membranes, wherein one thereof is porous and serves for protection against water condensation, has established itself as standard in the construction of oxygen sensors.

U.S. Pat. No. 4,664,119 describes an oxygen sensor comprising a housing, a cathode, a diffusion barrier, contact wires and an anode consisting of a tin-containing alloy. Acetic acid, tartaric acid, citric acid, malic acid, oxalic acid and salt acid are suggested as possible electrolytes. This sensor is designed for the transcutaneous measurement of oxygen.

EP 1 593 962 describes an RoHS-compliant galvanic oxygen sensor whose anode is made of zinc or aluminum. In the application it is described that these materials are susceptible to corrosion and are stable only within relatively narrow pH values of the electrolyte. Moreover, it is known that the corrosion current increases steeply as the temperature increases, so that sensors of this kind have a strongly restricted service life when being used in relatively high temperature ranges. Moreover, hydrogen is formed due to the corrosion process, which hydrogen has to be removed from the sensor. This requires an involved construction of the sensor housing. Moreover, sensors of this kind have a relatively high response time.

A RoHS-compliant galvanic oxygen sensor with relatively small response time is described in US 2010/0252432. The sensor preferably comprises a tin anode. A chelate-forming agent, e.g. EDTA, is added to the electrolyte of this sensor. The chelate-forming agent is said to prevent the deposition of reaction products at the anode, which can in turn lead to a passivation of the anode surface. The electrolyte is highly alkaline and has a pH value of preferably more than 12. In addition to silver or platinum, preferably gold is used as cathode material. The gold is sputtered onto the diffusion membrane of the sensor. Tests have shown that concentrations of about 1 mol/l have to be used for keeping the sensor properties stable for several months. Whether or not these sensors reach a common minimum service life of two years is questionable. Moreover, it is questionable whether the electrolyte does not decompose during the service life of the sensor. Furthermore, sensors of this kind have a high cross-sensitivity to $CO_2$ and nitrous oxide ($N_2O$). Therefore, they are not suitable particular for a medical-technical use.

The cross-sensitivity is the sensitivity of a measuring device to quantities or values different from the measurand. The latter is the quantity to be measured. A quantity which is not the measurand but which influences the information about the measurand provided by the measuring device is called influencing value. It causes a change in the measured value if only because the influencing value changes. It should be an aim of each measuring device development to keep its cross-sensitivity low. Also incomplete selectivity, which occurs, e.g., in gas sensors, contributes to a cross-sensitivity. Gas sensors are often also responsive to concentrations of gases different from the gas to be detected.

A further RoHS-compliant galvanic oxygen sensor is described in WO 2013/039414. The sensor is operated by means of a capillary which limits gas entry as so-called "limiting current" sensor. It alternatively uses an alkaline or acid electrolyte, a cathode made either from platinum/carbon or from silver or gold and an anode made from antimony, bismuth or copper. It is a disadvantage of these material combinations that insoluble reaction products are formed, which must not block the reactive surfaces. It is very involved to guarantee this in terms of construction. It is a further drawback of the use of an acid electrolyte that due to the proton consumption of the chemical reaction an electrolyte volume of about 20 ml is necessary to guarantee a service life of two years. Because of the relatively large overall size, such a sensor is not backwards compatible with conventional galvanic sensors using a lead anode.

The application WO 2013/049752 relates to a sensor having a pure bismuth anode, an acid electrolyte and a sputtered gold cathode.

DE 10 2006 024 022 A1, of the applicant of the present application, relates to an RoHS-compliant galvanic gas sensor comprising a housing, a tin-containing anode, a diffusion barrier, a cathode and an electrolyte, wherein the electrolyte is preferably made of an aqueous solution of cesium salts or also from a phosphoric acid solution. According to a preferred embodiment, the tin-containing anode can moreover comprise silver and/or copper. Because of the small sensor current, sensors of this kind have an extremely long service life of four to five years. They can be offered with the corresponding integrated electric circuit in a manner backwards compatible with classic galvanic oxygen sensors. Moreover, they are characterized by a very low cross-sensitivity to $CO_2$ and, therefore, have proved themselves in various industrial applications for many years. However, such sensors partly have a clear cross-sensitivity to nitrous oxide and, therefore, are only of limited suitability in specific medical applications and other applications in which nitrous oxide is present in the measuring gas mixture.

In medical engineering, nitrous oxide is used for anesthetic purposes and supplied to the patient in the respiratory gas mixture. The oxygen concentration in such anesthetic gas mixtures is often measured by means of electrochemical sensors. Nitrous oxide is furthermore also contained in various industrial gas mixtures, for example in the food industry and in exhaust gas measurements of combustion engines.

It is assumed that this sensor's sensitivity to nitrous oxide is based on the contamination of the copper-containing cathode with traces of silver. In C. E. W. Hahn, Analyst, 1998, 123, 57R-86R it is described that nitrous oxide is reduced electrochemically at silver-containing surfaces. Already in the 1970ies, this has already led to malfunctions in gas and blood gas sensors. Own experiments show that already the slightest traces of silver, which are contained even in highly pure copper, can lead to cross-sensitivities of three to ten percent. Sensors of this kind therefore cannot be used in medical applications because in these applications the cross-sensitivity of the sensor to another gas must not be higher than 0.3% of the indicated oxygen value in accordance with the standard ISO 80601-2-55.

With the extension of the RoHS regulations also to medical devices and controlling and monitoring instruments starting in the middle of 2014, it is desirable to provide backwards compatible galvanic oxygen sensors, if possible. In particular in accordance with the standard ISO 80601-2-55, these sensors should have only minimum cross-sensitivities to nitrous oxide. So far, this has not been possible with the RoHS-compliant galvanic oxygen sensors described above.

Therefore, it is an object of the present invention to provide a novel galvanic oxygen sensor which is RoHS-compliant and preferably backwards compatible with the existing lead-containing sensors in its remaining electrical and geometric specifications and also its service life and preferably does not have a cross-sensitivity to nitrous oxide. Sensors of this kind cannot only be used in connection with the initial installation but they can also be used as replacement parts for the many instruments and devices in the market.

SUMMARY OF THE INVENTION

According to the invention, this object is achieved by the features of independent claim 1. Advantageous developments are shown in the dependent claims.

A prerequisite for the functioning of an electrochemical oxygen sensor is that a majority, preferably all of the oxygen molecules diffusing at the cathode are reduced electrochemically. However, this can only be achieved reliably if the anode is sufficiently electropositive, i.e. if sufficient electrons are available for the oxygen reduction. On the other hand, the anode material should not be too electropositive because otherwise hydrogen develops at the cathode. In this case, the sensor would consume itself quickly; moreover, a basic current would be present which interferes with the actual signal. The hydrogen development can be slightly influenced by the electrolyte composition and/or the composition or coating of the cathode, but only to a little extent.

The situation is even worsened by the temperature-dependency of the electrochemical potentials. The typical range of operation or admissible temperature range of the sensors lies between −20° and 60° C., i.e. includes a difference of about 80 Kelvin, in which the point of operation of the anode must lie stably. Otherwise, either hydrogen develops or oxygen is converted incompletely at the cathode, leading to a non-linearity of the oxygen signal.

A further risk relates to the corrosion resistance of the anode material in the electrolyte within a specific temperature range. The service life of sensors having a conventional design is presently two to three years, and the new RoHS-compliant sensors should preferably have at least the same service life. This service life can be achieved, e.g., if the metal is protected at the surface either by an oxide layer and/or by the formation of a low-solubility salt. The layer should preferably remain conductive during the entire service life of the sensor because otherwise the electrochemical reaction is restricted or stopped.

Also the implementation of the idea of an "adjustable" electrochemical potential by way of the alloy composition involves risks because alloys often tend to inter-metallic phases and the formation of eutectics. The latter in turn often have properties different from that of the homogeneous mixed phases.

For a galvanic oxygen sensor having an electrolyte and an anode, the equations of the electrochemical reactions are as follows:

Equation for the electrochemical process at the cathode in an alkaline electrolyte:

$$O_2 + 2H_2O + 4e^- \rightarrow 4OH^-$$ (equation 1a)

In an acid electrolyte, protons are used for the reduction of oxygen:

$$O_2 + 4H^+ + 4e^- \rightarrow 2H_2O$$ (equation 1b)

Equations for possible electrochemical processes at the anode being dependent on the local pH value at the anode surface:

$$Me + 4OH^- \rightarrow MeO_2 + 4e^- + 2H_2O$$ (equation 2a)

$$2Me \rightarrow 2Me^{2+} + 4e^-$$ (equation 2b)

Me represents a metal which can occur after oxidation in a divalent or a tetravalent oxidation state. According to equation 2a, the anode material is oxidized to an oxide, according to equation 2b it is accordingly oxidized to a soluble salt.

The electric current flowing over the galvanic cell is preferably linearly or almost linearly dependent on the oxygen partial pressure or the oxygen concentration. The electrochemically active area of the anode should preferably be larger than that of the cathode in order to guarantee a sufficient driving force of the reaction and avoid a concentration polarization at the surface of the anode.

Because of the specific character of the problem posed, information about suitable material combinations can be obtained from the literature unfortunately only to a limited extent. The required electrochemical properties can only be calculated approximately and, therefore, must be detected experimentally.

Surprisingly, two-substance alloys made of tin and silver or copper and in particular also three-substance alloys made of tin, silver and copper show excellent properties in both acid and alkaline electrolytes. Tin as pure metal leads in acid electrolytes to the formation of hydrogen at the cathode and, therefore, can be used only with alkaline electrolytes. Silver and copper contents in an alloy with tin, however, reduce already in slight concentrations the electropositive behavior of the tin considerably. It has turned out that already concentrations of 0.1 to 3% of silver and/or copper are sufficient for sufficiently reducing the hydrogen development over the entire temperature range. Also higher concentrations of silver or copper in the alloy are possible, in view of the yield of the material and also in view of the production costs, however, they are less interesting.

The alloys are to a large extent corrosion-resistant over the necessary temperature range and yield an electrochemical potential that is sufficient for reducing oxygen at the cathode. This is preferably achieved particularly well if copper is used as cathode material.

If relatively small sensor currents are desired, in the simplest case already a wire or a thin band is sufficient, which is preferably made of copper, is in contact with the electrolyte, lies directly behind the diffusion membrane and is provided with a contact wire which, e.g., leads to the outside through the housing. The contact wire can, e.g., be bonded in the housing, welded by means of ultrasound or thermally with the plastic material in order to prevent electrolyte from leaking out of the housing. Advantageously, the contact wire is guided such that as little as possible of its surface is in contact with the electrolyte. Since small amounts of oxygen are dissolved in the electrolyte, this area could contribute to the basic current of the sensor and adversely affect the sensor behavior in environments with low oxygen concentration.

Particularly small sensor currents allow a simple design of the anode contacts and at the same time increase the service life of the sensor. In principle, this allows very small overall sizes of the sensors in case no backwards compatibility with existing sensors is required.

Also the composition of the electrolyte influences the function of the sensor. In combination with the described anode materials, the best results are achieved with aqueous alkaline solutions of alkaline salts or alkaline earth metal salts. In addition to the good electrochemical properties, these solutions also have a slightly hygroscopic behavior which counteracts drying of the electrolyte in case of possible dry operating conditions of the sensor and thus contributes to a long service life of the sensor also under rough conditions.

Very good results are achieved, e.g., when using aqueous solutions of cesium salts, in particular cesium hydroxide, cesium carbonate, cesium hydrogen carbonate and cesium acetate or mixtures thereof. These salts are very well soluble in water, are partly hygroscopic and thus contribute to a long service life of the sensor. Because of the good solubility, with relatively high concentrations the content of oxygen dissolved in the electrolyte is reduced and, therefore, a quick response time and a clean baseline current behavior of the sensor are achieved. Comparable results can be achieved by using magnesium, sodium or potassium salts.

For reducing the undesired cross-sensitivity of such a sensor to nitrous oxide to an acceptable level, the catalytic activity of the silver impurities in the copper cathode must be blocked. For this purpose, catalytic poisons can be added in a targeted manner to the electrolyte and/or the cathode. In particular, in accordance with specific embodiments it is also possible to provide the catalyst poison in a separate component or in a separate fluid in the sensor, as long as the catalyst poison is in connection with the electrolyte or the cathode. Moreover, it is also possible to provide pure sulfur or a sulfur composition in the sensor as "catalyst poison dispenser". In other words, the catalyst poison is provided in the sensor in such a manner that it can reach the cathode (preferably in the course of a chemical reaction), preferably can reach the cathode via the electrolyte. Catalyst poisons chemically bind to the active centers of the catalyst and block them.

Basically, different substances such as, e.g., sulfur or sulfur-containing compositions, lead and lead compositions, quinolines, pyridines, halogenides or carbon monoxide are possible as catalyst poison according to the invention. However, the present invention is not restricted to the use of exactly one catalyst poison. For example, one, two or more catalyst poisons can be used in the sensor. A catalyst poison, in heterogeneous catalysts also contact poison, is a substance which permanently reduces or cancels the effect of a catalyst. Thus, it slows down a normally desired chemical reaction.

Chemical catalysts can be affected or destroyed by numerous substances including heavy metals, halogens, polymers, sulfur or carbon monoxide. Catalyst poisons are bound by the catalyst instead of the substance whose reaction it should accelerate. They thus block the adsorption capability of the large surfaces of the catalyst particles.

The poisoning of a catalyst can be desired for reducing the activity of a catalyst in a targeted manner for a specific reaction. Oxidation catalysts are poisoned in a targeted manner, for example in order to control the oxidation of primary alcohols to aldehydes and not oxidize them to carbon acids. By the targeted poisoning of reduction catalysts with sulfur compositions it can be achieved, e.g., that alkynes are hydrated to alkenes but not further to alkanes.

The effect of the catalyst poison according to the invention will be explained in more detail on the basis of the following example.

The copper-containing cathode material can contain traces of impurities, e.g., silver or other metals. These metals are reaction centers which can catalyze the reduction of nitrous oxide ($N_2O$) in the cathode:

$$N_2O + H_2O + 2e^- \rightarrow N_2 + 2OH^-$$

By the addition of sulfur-containing compounds, e.g., sodium thiosulfate, the impurities, e.g. silver, react with the sulfur species and form sulfides. The reaction will be explained in the following on the basis of silver and sodium thiosulfate:

formation of silver ions: $Cu_2O + 2Ag + H_2O \rightarrow 2Ag^+ + 2Cu + 2OH^-$ reaction with sodium thiosulfate: $Na_2S_2O_3 + 2Ag^+ \rightarrow Ag_2S_2O_3$ (instable) $+ 2Na^+$ decomposition silver thiosulfate: $Ag_2S_2O_3 + 2OH^- \rightarrow Ag_2S + SO_4^{2-} + H_2O$ Because of the sulfide formation, e.g., the reaction centers of the silver impurities are inactivated. Thus, the reduction of nitrous oxide at the cathode can be suppressed. Because of an oxide layer on the cathode and the different potential as compared to the silver impurity, this reaction does not take place or takes place in a suppressed manner at the copper of the cathode. This means that the desired reduction of the oxygen to be measured at the copper cathode takes place in an almost unimpaired manner.

In particular, the present invention relates to a galvanic oxygen sensor comprising a housing, a cathode, a tin-containing anode, a diffusion barrier and an aqueous electrolyte with metal salts. Preferably, at least one catalyst poison is added to the electrolyte and/or the cathode. Alternatively or additionally, the sensor can also have a separate component or a separate fluid with catalyst poison, wherein the component or the fluid is preferably in connection with the electrolyte or the cathode.

The catalyst poison reduces or prevents preferably the decomposition of nitrous oxide at the cathode. The oxygen sensor according to the invention can be used, e.g., in medical technology, in particular can be applied in anesthetic machines, incubators and/or ventilators. However, the oxygen sensor according to the invention can also be used in industrial gas metrology, in particular can be applied for emission measuring and/or food technology.

The galvanic oxygen sensor has preferably a cross-sensitivity to nitrous oxide of at most 0.3% of the indicated oxygen value.

According to a preferred embodiment, the catalyst poison is a sulfur-containing composition, in particular (pure) sulfur, or one or more sulfur-containing compositions such as thiosulfate and/or polysulfide. Preferably, the sulfur, thiosulfate and/or polysulfide content in the electrolyte and/or in the cathode lies between 0.0001 and 10%. In particular, the thiosulfate and or polysulfide content in the electrolyte and/or the cathode can lie between 0.0001 and 10%, preferably in the range of 0.01 to 10%, 0.1 to 10%, 1 to 10%, 0.0001 to 5%, 0.0001 to 2% or 0.0001 to 1%.

Preferably, the sulfur, thiosulfate and/or polysulfide content in the component lies between 0.0001 and 30%. In particular, the thiosulfate and/or polysulfide content in the component lies between 0.0001 and 30%, preferably in the range of 0.01 to 30%, 0.1 to 30%, 1 to 30%, 0.0001 to 15%, 0.0001 to 10%, 0.0001 to 5%, 0.0001 to 2% or 0.0001 to 1%.

Preferably, the catalyst poison is lead or a lead composition, wherein the lead content of the electrolyte, of the component and/or of the cathode is preferably at most 0.1%.

Preferably, the catalyst poison (4) can be quinoline and/or halogenide and/or carbon monoxide and/or pyridine.

Preferably, the electrolyte has a pH value greater than 7.

Preferably, the metal salts in the electrolyte are alkaline or alkaline earth metal salts, in particular magnesium, sodium, potassium or cesium carbonates or hydrogen carbonates and salts of their organic acids or a mixture of these substances.

According to a further preferred embodiment, the cathode comprises copper or a copper-coated component or a copper alloy.

According to a further preferred embodiment, the anode material comprises tin or tin alloys with silver and/or copper, wherein the total content of silver and copper is preferably at least 0.1% and at most 25% of the total mass, the copper content is preferably between 0.1 to 2%, 0.5 to 5%, 2 to 15% or 5 to 25% and the silver content is preferably between 0.1 to 2%, 0.5 to 5%, 2 to 15% or 5 to 25%.

According to a further preferred embodiment, the oxygen sensor comprises a nickel-containing contact wire at the anode.

Moreover, the present invention also relates to methods for measuring oxygen by means of a galvanic oxygen sensor according to the invention. For this purpose, additional evaluating electronics are used for evaluating signals of the oxygen sensor and converting them into an oxygen content.

In addition to using the galvanic sensor described above as oxygen sensor, it is also possible to use the cross-sensitivity to nitrous oxide, which the sensor has without the addition of a catalyst poison, for a targeted measurement of nitrous oxide. Preferably, a remaining cross-sensitivity to oxygen should be compensated for by suitable measures. For example, a second cathode having a lower cross-sensitivity to oxygen can be placed in the same electrolyte and the signal thereof can be offset against that of the first cathode. A further possibility is to place the second cathode in a mechanically limited second electrolyte space. In this case it is possible to use two different electrolytes in order to control the selectivity of the two cathode reactions differently. Also in this case, the two sensor signals are preferably offset against each other in order to compensate for the respective residual cross-sensitivity.

Oxygen sensors manufactured in this manner exhibit a stable and preferably linear signal behavior relative to the oxygen partial pressure over a wide temperature range. By the design of the cathode surface, the sensor current can be controlled such that it lies in the same order of magnitude as that of the previous sensors comprising lead anodes. Thus, there is a backwards compatibility with the devices in the market.

BRIEF DESCRIPTION OF THE DRAWINGS

In the following, preferred embodiments of the present invention are described in detail with reference to the Figures in which.

DETAILED DESCRIPTION OF PREFERRED EMBODIMENTS

Figure 1:
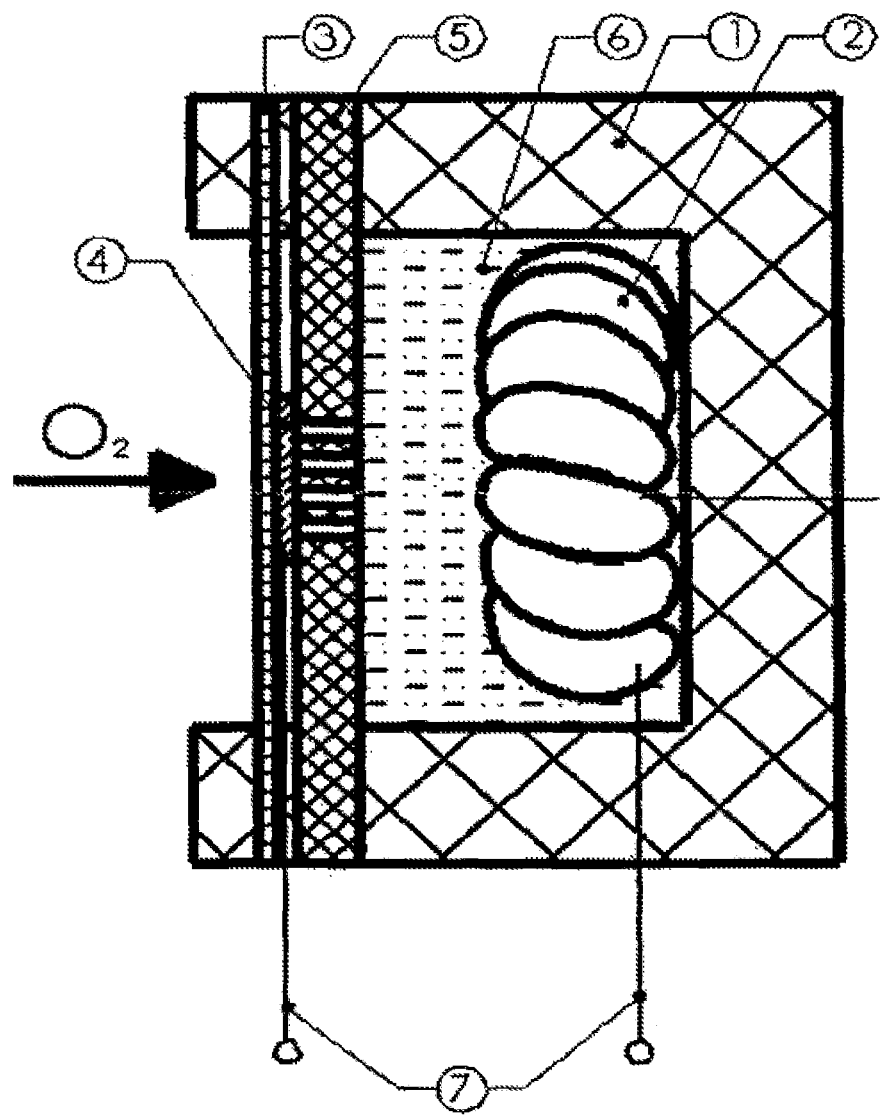
FIG. 1 shows a cross-sectional view of a galvanic oxygen sensor according to the invention.

A galvanic electrochemical oxygen sensor according to FIG. 1 comprises as essential components preferably a housing 1, a diffusion barrier 3, an anode 2 as well as a cathode 4. The anode 2 is preferably arranged in the housing 1 and made, e.g., from an alloy of tin with 3% copper, with a preferred weight of 2.5 g. The diffusion barrier 3 forms a boundary layer to the measuring gas environment, i.e. to the outside, and is exemplarily made as diffusion membrane 3 of polytetrafluoroethylene. The cathode 4, preferably made of a flat wire of copper, is arranged, e.g., behind the diffusion membrane 3 on a base 5. An electrolyte 6 is preferably arranged between the cathode 4 and the anode 2, preferably between the base 5 and the anode 2. Preferably, the electrolyte 6 surrounds a large part of the anode 2. The electrolyte 6 is, e.g., an aqueous solution with 20% cesium carbonate, 10% cesium hydrogen carbonate and 1 g/l sodium thiosulfate with a pH level of about 10. The contacts 7, which are connected to the anode and the cathode, are preferably led to the outside in order to provide an electric current flow which is at the same time the measurand. The electric current flowing over the resistor is preferably proportional or approximately proportional to the oxygen partial pressure at the diffusion membrane. The cathode 4 has, e.g., a surface of 2.5 mm$^2$. With a 25 μm thick diffusion membrane 3, a sensor signal of 3 μA is obtained in air. During gassing with nitrogen ($N_2$), the signal decreases to about 7.5 nA. During gassing with oxygen ($O_2$), approximately the theoretical value of 14.3 μA is obtained.

The oxygen diffused through the diffusion membrane 3 reaches the cathode 4 where it is reduced. At the anode 2, metal ions are dissolved in solution or the metal turns to metal dioxide in accordance with Faraday's law. In the preferred embodiment shown in FIG. 1, the catalyst poison of the invention is added to the electrolyte 6. However, the present invention is not restricted to this embodiment. For example, alternatively or additionally catalyst poison can be added to the cathode 4. According to a further embodiment that is not shown, catalyst poison can be provided alternatively or additionally in a separate fluid and/or in a separate component, preferably within the sensor, in order to prevent or reduce the dissolution of nitrous oxide at the cathode 4. Preferably, the separate component or separate fluid is in connection with the electrolyte 6 and/or the cathode 4.

Figure 2:
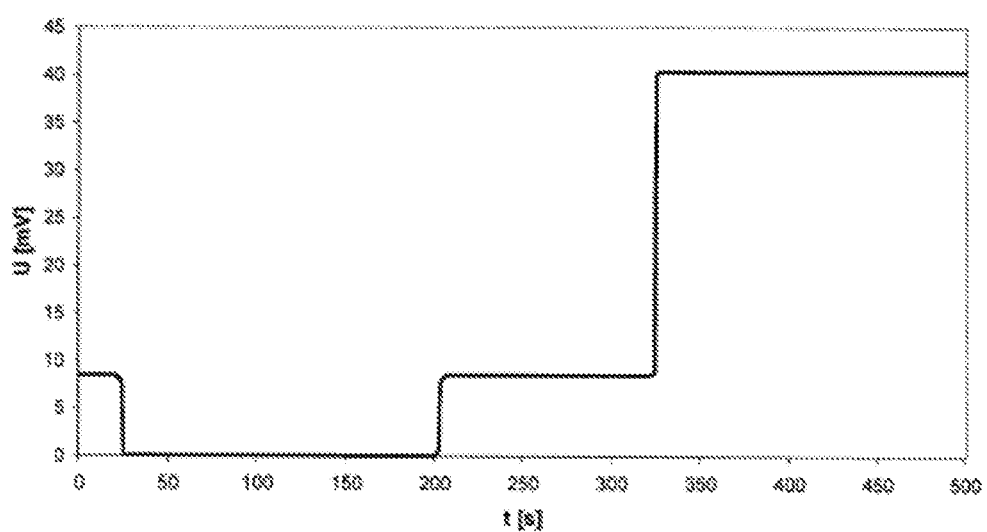
FIG. 2 shows the dependency of a sensor signal on the oxygen partial pressure.

As shown in FIG. 2, an oxygen sensor manufactured in this manner has an excellent linearity relative to the oxygen partial pressure. The signal sequence shows the voltage of the sensor during gassing with air, with nitrogen, with air and with 100% oxygen. The oxygen signal is about 4.8 times greater than the air signal and thus corresponds to the theoretical value.

Figure 3:
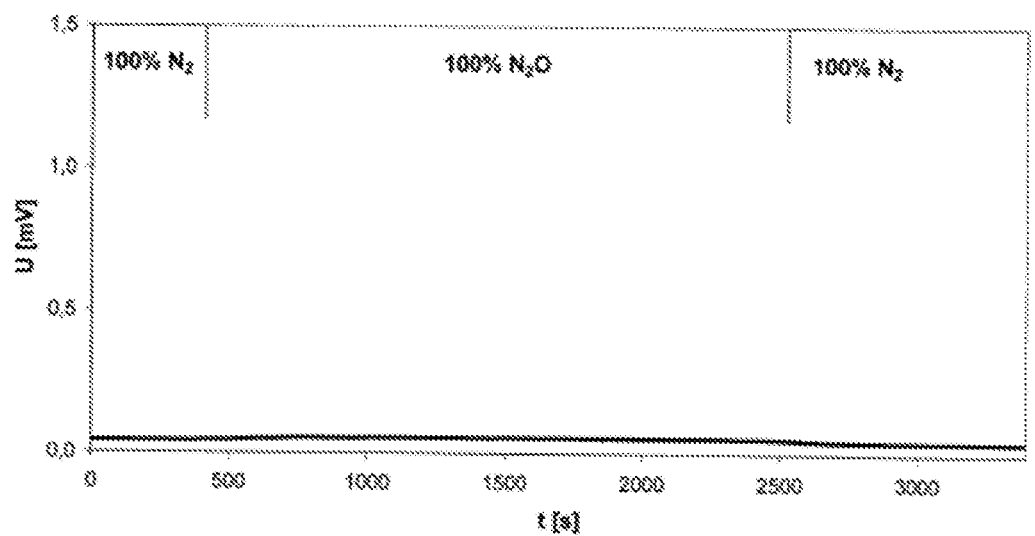
FIG. 3 shows the signal behavior of a sensor according to the invention during gassing with 100% nitrous oxide.

FIG. 3 shows that an oxygen sensor manufactured in this manner does not have a noteworthy cross-sensitivity to nitrous oxide. The signal sequence shows the voltage of the sensor successively during gassing with nitrogen, with nitrous oxide and with nitrogen.

Figure 4:
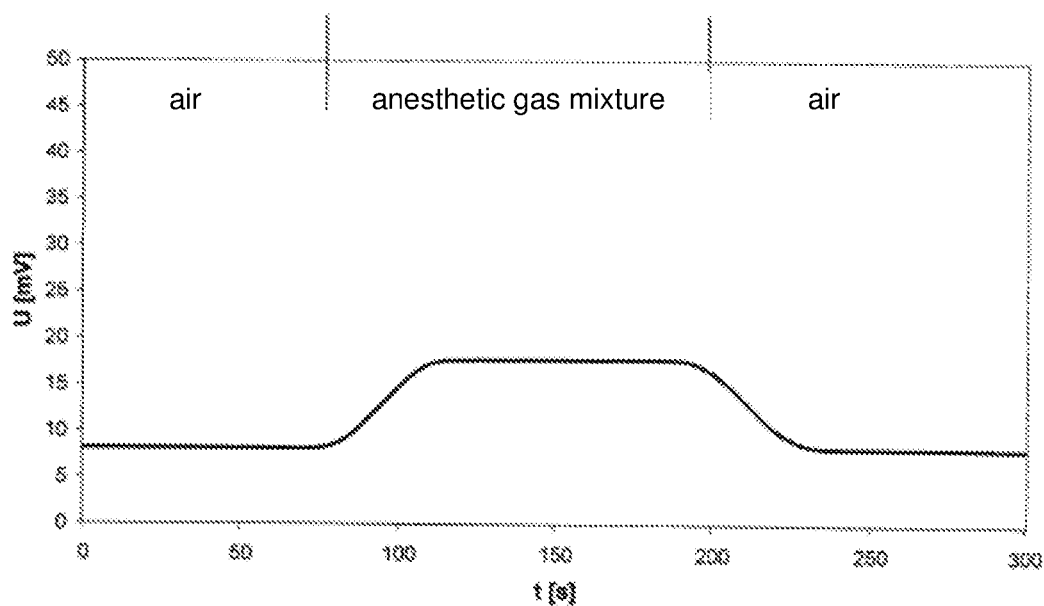
FIG. 4 shows the behavior of a sensor according to the invention during gassing with a gas mixture comprising 45% oxygen, 5% carbon monoxide, 48.5% nitrous oxide and 1.5% isoflurane.

Also in connection with the measurement in an anesthetic gas mixture comprising 48.5% nitrous oxide, 45% oxygen, 5% carbon dioxide and 1.5% isoflurane, the sensor does not show a noteworthy cross-sensitivity when considering the mixing error of the test gas. The signal sequence of FIG. 4 shows the voltage of the sensor successively during gassing with air, with the anesthetic gas mixture and with air.

The invention also comprises the exact expressions, features, numeric values or ranges, etc. if above or in the following these expressions, features, numeric values or ranges are mentioned in connection with expressions such as, e.g., "approximately, about, around, substantially, generally, at least, minimum", etc. (i.e. "about 3" should also comprise "3" or "substantially radial" should also comprise "radial"). The German expression "bzw." also means "and/or".

The invention claimed is:

1. A galvanic oxygen sensor for determining an oxygen content, the galvanic oxygen sensor comprising:
a housing, a cathode, a tin-containing anode, a diffusion barrier and an aqueous electrolyte with metal salts,
wherein the cathode is made of copper or a copper-coated component or a copper alloy,
wherein a copper material of the cathode is in direct contact with the electrolyte, and
wherein the oxygen sensor comprises at least one catalyst poison in the electrolyte and/or cathode which prevents or reduces the decomposition of nitrous oxide at the cathode based on impurities of silver or other metal impurities in the copper cathode,
wherein the at least one catalyst poison is pure sulfur or a sulfur-containing component comprising thiosulfate and/or polysulfide, and
wherein the galvanic oxygen sensor is configured to operate while avoiding an operating potential.

2. The galvanic oxygen sensor according to claim 1, wherein the electrolyte and/or a fluid which is in connection with the electrolyte and/or the cathode comprises the at least one catalyst poison.

3. The galvanic oxygen sensor according to claim 1 for application in medical engineering.

4. The galvanic oxygen sensor according to claim 1 for application in industrial gas metrology.

5. The galvanic oxygen sensor according to claim 1 whose cross-sensitivity to nitrous oxide is at most 0.3% of the determined oxygen content.

6. The galvanic oxygen sensor according to claim 1, further comprising lead or a lead composition as an additional catalyst poison.

7. The galvanic oxygen sensor according to claim 1, wherein the electrolyte has a pH value greater than 7.

8. The galvanic oxygen sensor according to claim 1, wherein the metal salts in the electrolyte are alkaline or alkaline earth metal salts, sodium, potassium, cesium carbonates, hydrogencarbonates and salts of their organic acids, or a mixture of these substances.

9. The galvanic oxygen sensor according to claim 8, wherein the alkaline earth metal salt comprises magnesium.

10. The galvanic oxygen sensor according to claim 1, wherein the anode material comprises tin or tin alloys with silver and copper, wherein:
the copper content lies between 0.1 to 2%, 0.5 to 5%, 2 to 15% or 5 to 24.9% of the total mass of the anode material;
the silver content lies between 0.1 to 2%, 0.5 to 5%, 2 to 15% or between 5 to 24.9% of the total mass of the anode material; and
the total content of silver and copper is at least 0.1% and at most 25% of the total mass of the anode material.

11. The galvanic oxygen sensor according to claim 1, wherein the oxygen sensor comprises a nickel-containing contact wire at the anode.

12. The galvanic oxygen sensor according to claim 1 for use in an anesthesia machine, incubator, and/or ventilator.

13. The galvanic oxygen sensor according to claim 1 for application in emission measurement or food technology.

14. A method for measuring oxygen comprising the steps:
providing the galvanic oxygen sensor according to claim 1,
providing evaluation electronics for evaluating signals of the galvanic oxygen sensor; and
determining an oxygen content using the galvanic oxygen sensor and the evaluation electronics while avoiding an operating potential.

15. A method of producing the galvanic oxygen sensor according to claim 1, the method comprising:
providing the housing, the cathode, the tin-containing anode, the diffusion barrier and the aqueous electrolyte with metal salts, such that the copper material of the cathode is in direct contact with the electrolyte; and
poisoning the cathode or electrolyte in the galvanic oxygen sensor with the at least one catalyst poison.

16. The method of claim 15, wherein the galvanic oxygen sensor possesses a cross-sensitivity to nitrous oxide of at most 0.3% of the determined oxygen content.

17. A galvanic oxygen sensor for determining an oxygen content, the galvanic oxygen sensor comprising:
a housing, a cathode, a tin-containing anode, a diffusion barrier and an aqueous alkaline electrolyte,
wherein the cathode is made of copper or a copper-coated component or a copper alloy,
wherein a copper material of the cathode being is in direct contact with the electrolyte, and
wherein the aqueous alkaline electrolyte comprises alkaline metal salts and a catalyst poison,
wherein the alkaline metal salts are selected from the group consisting of magnesium carbonate, sodium carbonate, potassium carbonate, cesium carbonate, hydrogen carbonates or a mixture thereof, and
wherein the catalyst poison is pure sulfur or a sulfur-containing component comprising thiosulfate and/or polysulfide.

* * * * *